United States Patent [19]

Henley

[11] Patent Number: 5,569,178
[45] Date of Patent: Oct. 29, 1996

[54] POWER ASSISTED SUCTION LIPECTOMY DEVICE

[76] Inventor: Julian L. Henley, 330 Orchard St., New Haven, Conn. 06511-4417

[21] Appl. No.: 546,478
[22] Filed: Oct. 20, 1995
[51] Int. Cl.[6] .................................................. A61B 17/20
[52] U.S. Cl. ................................................................ 604/22
[58] Field of Search ...................... 604/22; 606/167–174; 128/751–759

[56] References Cited

U.S. PATENT DOCUMENTS

| | | | |
|---|---|---|---|
| 4,167,944 | 9/1979 | Banko | 606/170 |
| 4,662,869 | 5/1987 | Wright | 604/22 |
| 4,819,635 | 4/1989 | Shapiro | 604/22 |
| 4,867,157 | 9/1989 | McGurk-Burleson et al. | 606/170 |
| 4,932,935 | 6/1990 | Schwartz | 604/22 |
| 5,084,052 | 1/1992 | Jacobs | 606/170 |
| 5,242,460 | 9/1993 | Klein et al. | 604/22 |
| 5,383,884 | 1/1995 | Summers | 606/170 |
| 5,403,334 | 4/1995 | Evans et al. | 606/159 |

*Primary Examiner*—Manuel Mendez
*Attorney, Agent, or Firm*—Michael G. Petit

[57] ABSTRACT

A power assisted liposuction handpiece including a handle portion and a cannula portion. The cannula portion includes an apertured outer tube having a rotary auger disposed within the outer tube. In a preferred embodiment, a portion of the rotary auger beneath the aperture has an elastically deformable outer tissue-contacting edge. The elastically deformable outer tissue-contacting edge avulses or tears apart fatty tissue protruding through the aperture into the cannula when the auger rotates. The rotating auger also facilitates the mechanical transport of the avulsed cells to a vacuum aspirator port within the handpiece for removal. The relatively soft, elastically deformable tissue-contacting edge of the auger reduces trauma to more cohesive non-fatty neural and vascular tissue providing greater tissue selectivity than present invasive liposuction equipment. In addition, the handpiece is relatively easy to use, rendering the procedure less tiring for the surgeon. In an alterative embodiment, the avulsing peripheral edge of the cannula aperture is elastically deformable, permitting avulsion of fatty tissue having a relatively low tensile strength but capable of deforming under pressure thereby preventing avulsion of more tenacious tissue. In still another embodiment, the shaft of the rotating member is elastically deformable to permit high tensile strength tissue to deflect the rotating tissue-contacting edge of the auger or similar avulsing rotary member when such tenacious tissue is pinched between the edge of the cannula aperture and the tissue-contacting edge of the rotating member.

5 Claims, 2 Drawing Sheets

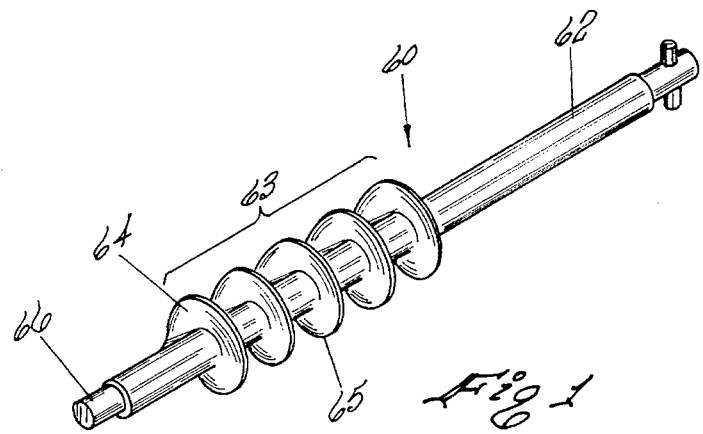
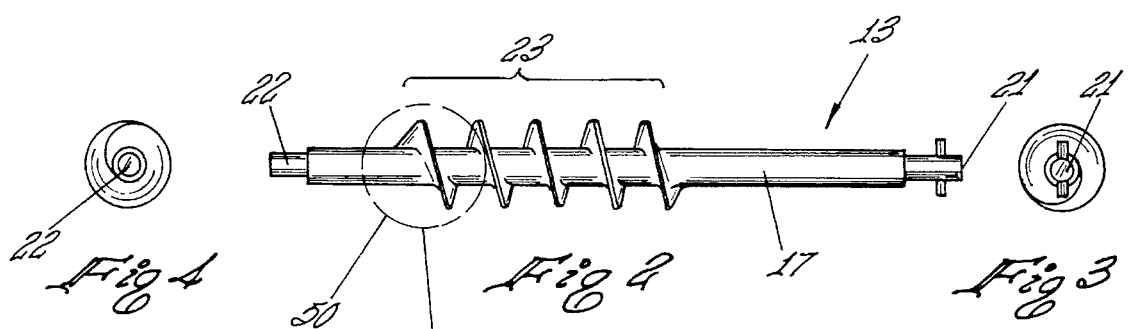
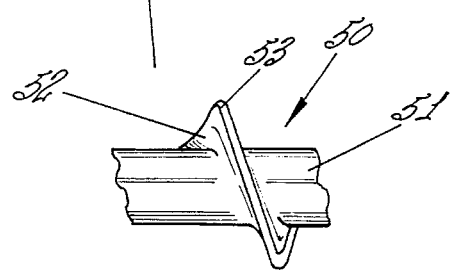
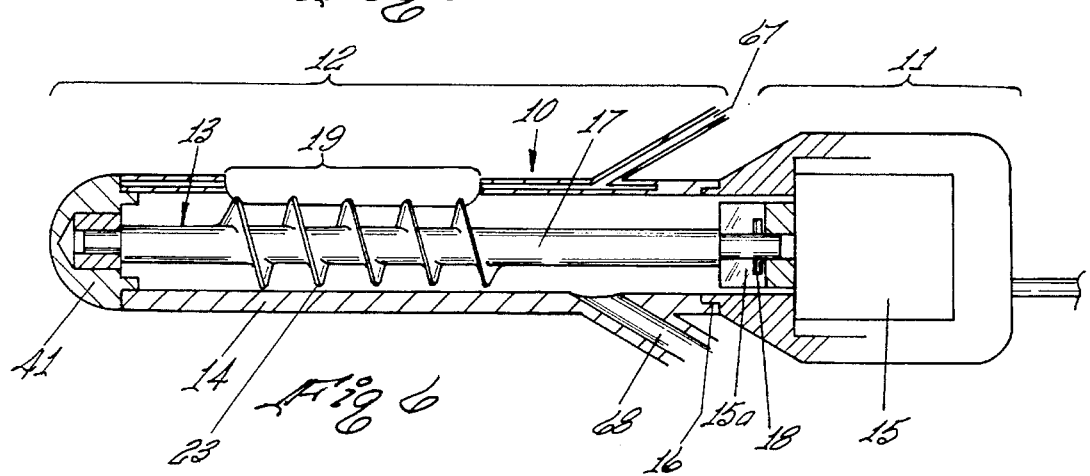

POWER ASSISTED SUCTION LIPECTOMY DEVICE

BACKGROUND OF THE INVENTION

1. Field of the Invention

An apparatus for the selective removal of fatty tissue beneath the skin of an animal and, more particularly, to a handpiece for a power assisted suction lipectomy device.

2. Prior Art

Suction assisted lipectomy, a procedure originally developed in France, was introduced to the United States over a decade ago. Since then, the procedure has rapidly spread in popularity and consumer demand. The procedure involves anesthetizing a portion of the body containing unwanted fat deposits, introducing an apertured suction cannula beneath the skin into the unwanted fat and tearing the tissue apart by repeatedly jabbing the tip of the cannula into the tissue thereby mechanically breaking up (avulsing) the fat. The avulsed fat cells are then aspirated by suction means. Continuous reciprocal stroking of the cannula mechanically disrupts fatty tissue, allowing additional fat to be removed. The repetitive stroking movement of a cannula is both tiring for the physician and traumatic and uncomfortable for the patient who, notwithstanding anesthesia, experiences pain and discomfort with each thrust. Since fat from various different portions of the body is normally removed during the procedure, and further in view of the intense discomfort of the procedure, adequate local anesthesia of every fat-containing operative site may not be achieved.

Several liposuction cannulas, some disposable and some reusable, are commercially available. Liposuction cannulas are provided in different lengths and diameters, each having different slot or aperture dimensions to meet particular needs. Some apertures are configured in the "cobra head" configuration to increase the surface area of the cannula aperture while other cannulas have several openings on the side of the cannula. In each case the metal cannula is introduced into the (anesthetized) fat bearing target area through an incision in the skin. Powerful suction pulls some of the surrounding fat into the hollow cannula through one or more slots or apertures and the thrusting movement of the cannula avulses a portion of such fat. Adipose tissue has a low tensile strength compared to other tissues with which it is associated and the repetitive back and forth thrusting movement of the suction cannula preferably and differentially avulses large portions of fat from a given surgical area. This technique exploits the lower tensile strength of the fatty tissue and relatively spares the blood vessels from perforation since vascular structures comprise thicker collagen and have greater tensile strength than fatty tissue.

Numerous power assisted lipectomy devices have been developed. Some such power assisted devices employ mechanical shearing devices deployed at or near the distal tip of the cannula to cut the tissue. Others employ a cannula transmitting ultrasonic vibrations to the operative site to disperse or rupture the cells adjacent to the cannula. A power assisted suction lipectomy device employing a rotary member housed within a cannula is described by Swartz in U.S. Pat. No. 4,932,935, the teachings of which patent is hereby incorporated herein by reference thereto. Swartz, in the aforesaid '935 patent, discloses an improved lipectomy device which includes a cannula having an inner rotatably mounted tube and a concentric outer tube. The outer tube, the surface of which contacts the tissue during lipectomy, has an elongate slot in the wall thereof. The inner tube, which is rotatably mounted within the outer tube, has a spiral slot in the wall thereof A motor housed within the handle of the cannula rotates the inner tube within the outer tube by means of a worm drive. The spiral slot of the inner tube, which underlies the elongate slot on the outer tube, presents a "moving hole" when viewed from outside the cannula. The "moving hole" provides a moving aperture through which fatty tissue surrounding the cannula may enter the inner tube thereafter to be pulled apart from surrounding tissue. The avulsed tissue is aspirated from the operative site through the hollow interior of the inner tube of the cannula into a removal port by suction means.

In an alternate embodiment, Swartz (U.S. Pat. No. 4,932,935) discloses a cannula wherein the elongate slot in the outer cannula, which slot is disposed substantially coaxially with the long axis of the cannula, overlies a diagonal slot in the inner tube. Motor means within the handle of the cannula drives the inner tube in a rotary oscillatory motion with respect to the outer tube causing the "traveling hole" to move back and forth within the slot of the outer cannula rather than appearing at one end of the slot and disappearing at the other end only to reappear at the first end of the slot upon completion of a full rotation. The edges of the slots on both the inner and the outer tubes are provided with rounded edges to prevent unnecessary cutting of tissue. The rotund metal edges bordering the slots on the inner and the outer tubes pinch tissue which projects therebetween. This pinching and pulling avulses a portion of the tissue without applying sufficient force to avulse tissue having higher tensile strength. The Swartz device reduces trauma to the patient by preserving the integrity of non-target tissue while providing enhanced selectivity for removing fatty tissue.

The above described cannulas, with or without ultrasonic assistance, remain the mainstay of the suction lipectomy surgical instrumentarium and such improved cannulas allow the operating surgeon (through multiple strokes with the suction assisted cannula) to remove fat more or less differentially; sparing the larger blood vessels from injury. Although smaller blood vessels are traumatized by the force required for avulsion of fat and a certain amount of bleeding is expected, this elective procedure has generally proven itself to be relatively safe and effective in accomplishing the localized removal of fat in patients. Still, there exists a need for a power assisted liposuction handpiece which further reduces trauma to non-fatty tissue and is less tiring to use.

SUMMARY OF THE INVENTION

The present inventor has employed power assisted liposuction handpieces to facilitate suction lipectomy, and more particularly, has used ultrasound at power levels up to 150 watts as an adjunctive means for facilitating lipectomy and for reducing trauma to non-fatty tissue during the procedure. Although ultrasonic-assisted devices are capable of breaking or rupturing cells, the number of such ruptured the cells does not significantly add to the overall removal of the fat. The marginal improvement in tissue specificity gained while employing ultrasonic assistance during liposuction dramatizes the need for more efficient power assisted suction lipectomy equipment. Accordingly, the present power-assisted suction lipectomy handpiece provides improved tissue specificity during fat removal and ease of operation by employing a liposuction handpiece comprising, in combination, a handle portion and a cannula portion releasably attached to the handle portion. The cannula portion further comprises an apertured outer housing and a rotary member. The rotating members together with the cannula, apertured outer tube cooperate to avulse or pull apart tissue protruding into the cannula through the aperture in the outer tube. The stationary edge of the aperture and the rotating tissue-contacting edge of the rotating member pinch and stretch the tissue until the tissue pulls apart. The present invention employs an elastically deformable avulsing member.

The handpiece has a high torque variable speed electrical motor housed within the handle portion of the handpiece. Alternatively, a rotating cable from an external motor may pass through the handle portion. In any case, the cable or motor supplies rotational energy to the distal end of the handle portion by means of a drive shaft. The motor drive shaft engages the shaft of a rotating member (such as an auger) rotatably mounted within an elongate invasive apertured outer tube portion of the cannula. The handle portion of the device, to which handle portion the cannula is attached, includes connector means for providing electrical power to the motor as well as means for attachment to a high vacuum tubing and a hose connection nipple for delivering an irrigation solution to the handpiece for subsequent transport through the handpiece to the operative site.

The vacuum connection port and irrigating fluid connection port, which irrigating fluid connection port is in fluid communication with the distal (invasive) end of the cannula, are preferably mounted on the proximal (non-invasive) end of the cannula portion or mounted upon the handle portion of the handpiece. The handpiece may advantageously include a temperature conducting heat sink-type of material on the handle portion of the handpiece overlying the electric motor to dissipate intraoperative heat generated by the rotary movement of the high torque variable speed motor housed within the handle.

During liposuction, a sterile pressurized irrigation solution enters an irrigating lumen within the apertured outer tube of the cannula through an irrigating fluid connector port located at the proximal end of the cannula portion, thereafter to be conducted through the lumen and discharged at the operative site near the distal tip of the cannula. The irrigating fluid preferably exits the cannula at or near the aperture in the cannula to provide lubrication for the mechanical parts and facilitate transport of the fragments of avulsed fat from the operative site through the cannula to the aspiration port.

Within the confines of the hollow, elongate, apertured tube comprising the outermost portion of the cannula, an auger is rotatably mounted coaxially with the cannula. The shaft of the auger is connected directly to the rotating shaft of the rotary motor housed within the handle portion of the device. The auger, which is disposed within the outer apertured tube portion of the cannula, is positioned so that at least a portion (the avulsing portion) of the auger underlies the aperture. In one embodiment of the handpiece, the outermost tissue-contacting edge of the portion of the auger underlying the aperture is an elastic polymer. The avulsing outer edge of the avulsing portion of the auger underlying the cannula aperture, preferably has a spiral shape, similar to a corkscrew.

When the apertured cannula portion of the lipectomy device penetrates unwanted fatty tissue, the surgeon presses upon the overlying skin, the pressure forcing a portion of the fat adjacent to the aperture to bulge or herniate through the aperture into the interior of the cannula. The auger, rotating therewithin, presents an elastic tissue-contacting avulsing edge which grasps and avulses, or pulls apart, fatty tissue caught between the moving avulsing edge of the auger and the perimeter of the aperture while sparing more cohesive tissue. The auger can also serve as an inner tube portion of the cannula if provided with a second aperture to produce the shearing forces necessary to avulse fat protruding through both the inner tube (rotating member) aperture and the outer tube aperture. The rotary motion of the spiral shaped auger further facilities the transport of the avulsed fat away from the operative site and through the cannula towards the vacuum port. As the cannula is introduced into a subcutaneous fat-bearing area, instead of the surgeon applying a reciprocal back and forth movement to avulse fat, the electric-powered rotary motion of the auger within the cylindrical apertured outer tube of the cannula produces a gradual controlled avulsion of fat cells protruding into the cannula through the aperture.

In view of the foregoing summary of the invention, it is a primary object of this invention to provide an improved handpiece for a power assisted suction lipectomy device operable for removing fat from beneath the skin of an animal.

It is another object of the invention to provide a handpiece for a power assisted lipectomy device which, in operation, selectively removes fatty tissue thereby reducing trauma to non-fatty tissue.

It is still another object of the invention to provide a handpiece for a power assisted suction lipectomy device which reduces damage to nerves and vascular tissue during suction lipectomy.

It is yet another object of the invention to provide a handpiece for power assisted liposuction which reduces both heat generation within the handpiece and power loss during suction lipectomy.

Further objects, features and advantages of the invention will become apparent upon consideration of the following detailed disclosure of the invention especially when it is taken in conjunction with the accompanying drawings wherein:

BRIEF DESCRIPTION OF THE DRAWINGS

FIG. 1 is a perspective view of an embodiment of the elastically deformable rotary member of the handpiece in accordance with the present invention.

FIG. 2 is a side elevational view of the elastically deformable rotary member of FIG. 1.

FIG. 3 is an end on view of the rotary member of FIG. 2 viewed in the direction from right to left.

FIG. 4 is an end view of the rotary member of FIG. 2 viewed from left to right.

FIG. 5 is an enlarged view of a section of the auger portion of the rotary member shown in FIG. 2, showing the elastically deformable tissue-contacting surface on the outer edge of the auger flanges.

FIG. 6 is a partially cut-away side view of the power assisted suction lipectomy handpiece of the present invention showing the handle portion, the cannula portion, including vacuum aspiration and irrigating ports.

FIG. 9a is an end on view of the rotary member of FIG. 8 viewed from right to left showing means for releasably connecting the proximal end of the rotary member of the cannula portion of the handpiece to the distal end of the motor shaft projecting from the handle portion of the handpiece.

FIG. 9b is an end view of the drive shaft rotary power source housed within the handle portion of the handpiece operable for matingly and releasably engaging the proximal end of the rotary member shown in FIG. 9a.

DESCRIPTION OF THE PREFERRED EMBODIMENTS

Figure 7:
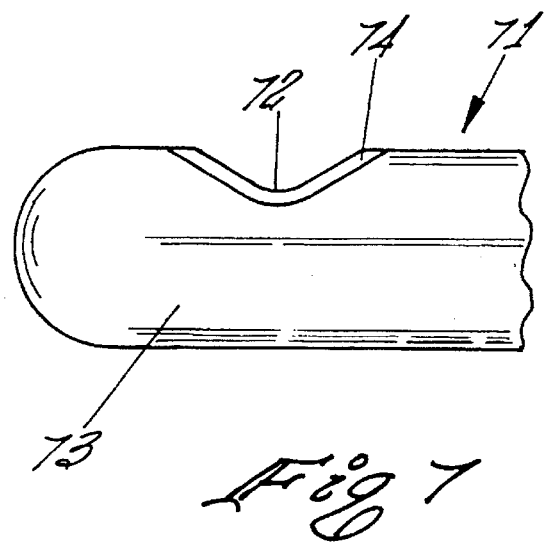
FIG. 7 shows a side elevational view of a second embodiment of a handpiece in accordance with the invention wherein the avulsing edge of the aperture in the outer tube of the cannula is elastically deformable.

With reference first to FIG. 6, a handpiece 10 for performing power-assisted suction lipectomy in accordance with the present invention is shown. The handpiece 10 comprises a handle portion 11 and a cannula portion 12. The cannula portion 12 comprises a rotary member 13 rotatably mounted within an elongate apertured outer tube 14. A rotary motor 15 for driving the rotary member 13 is housed within the handle portion 11 of the handpiece 10. Alternatively, a pneumatically or vacuum driven motor operable for supplying of rotational power may be used to rotate the rotating member 13 (also referred to herein as an "auger"). A cable drive shaft from an external motor may also be employed to deliver rotary power to the rotating member. The speed of rotation of the rotary motor 15 is preferably controlled by a foot operable controlling means (not shown). Such speed control devices are well known in the art. The cannula portion 12 of the handpiece 10 is affixed to the handle portion 11 of the handpiece 10 by means of a releasable connector 16. The rotary member 13 housed within the cannula portion 12 has a central shaft 17 having coupling means 18 on the proximal end of the shaft 17 operable for releasably attaching the shaft 17 of the rotary member 13 to the drive shaft connector means 15a on the distal end of the drive shaft of the motor 15 within the handle portion.

A side elevational view of the rotatable member 13 of the cannula portion 12 of the handpiece 10 is shown in FIG. 2. The rotary member 13 comprises as an auger having a shaft 17 with a proximal end 21 and a distal end 22 and auger portion 23. The auger portion 23 of the rotary member 13 is dimensioned to be at least as long as the overlying aperture 19 in the outer tube portion 14 of the cannula. The proximal end of the auger portion, as shown in FIG. 3, has releasable connector means 21 thereon operable for attachment to mating attachment means 15 on the distal end of the drive shaft of the rotary motor (not shown in FIG. 2).

FIG. 4 is an end-on view of the rotary member of FIG. 2, viewed from left to right, showing the distal end of the rotating member 13. A stabilizing bearing 22 on the distal end of the auger shaft rotatably engages a bearing seat 41 axially mounted on, and integral with, the outer tube 14 of the cannula 12 which bearing 22 provides support for the rotary member 13.

An embodiment of the rotary member 13 showing a particular auger portion in detail is presented in FIG. 5. In this embodiment, the auger portion 50 is positioned upon the shaft 51 of the rotary member 13 so that the auger portion will underlie the aperture (not shown) in the outer tube (not shown in FIG. 5) of the cannula portion of the handpiece. The auger 50 comprises a shaft 51 having a spiral shaped flange 52 mounted thereon and projecting laterally therefrom, the flange 52 terminating in a tissue-contacting edge 53. The tissue-contacting avulsing edge 53 is elastically deformable, undergoing distortion or deflection when pressure is applied thereto. The thickness and taper of the flange 52 between the shaft 51 and the avulsing edge 53 may be varied to construct a variety of augers having various elasticity and avulsing efficiency and specificity for fatty tissue. For example, for an auger having a flange 52 comprising a particular elastomer composition, a short thick flange having little lateral extension from the shaft will be less elastic than a thin flange with greater lateral projection.

An elastically deformable tissue-contacting edge 53 may merely comprise a layer of rubber or similar elastomer coating the avulsing edge of a boring auger. The tissue-contacting edge 53 of the flange 52 may additionally and advantageously have small parallel grooves (not shown) or similar texture on the surface thereof. These grooves preferably extend proximally (inwardly) from the distal portion of the avulsing edge 53, traversing the avulsing edge at an angle of about 45°–90° to the avulsing edge 53. The grooves or similar texture serve to roughen the avulsing tissue-contacting edge of the avulsing portion of the auger (the portion of the auger underlying the aperture in the outer tube), enhancing the ability of the rotating avulsing edge 53 to grasp the fatty tissue. In operation, grooving or texturing the avulsing edge 53 improves the removal efficiency of any fatty tissue captured between the corrugated avulsing edge 53 of the rotating auger and the stationary avulsing edge of the cannula aperture. While the particular contour, length and shape of the grooves or corrugations in the avulsing edge of either the auger or the aperture may vary, the density of such grooves is preferably between 1 and 30 grooves per millimeter along the periphery of the avulsing edge providing such corrugations and/or texture enhances the ability of the avulsing edge to grip the tissue, the firmer grip enabling more efficient avulsing of tissue.

In another embodiment of the handpiece, the entire flange of the auger can be fabricated as a spiral shaped portion from a flexible polymer such as polyethylene or PTFE selected to be stable at operative cannula temperatures. In still another embodiment, the entire rotary member, including the auger and the shaft, can be fabricated from an elastically deformable thermostable elastomer material such as high durometer silicone rubber, polyethylene or a polyhalogenerated hydrocarbon polymer such as PTFE. The important feature of the handpiece is that the avulsing portion of the cannula is capable of elastic deformation. The elasticity of the avulsive portion of the cannula (that is, the portion of the cannula comprising the tissue-contacting corrugated avulsing edge of the rotary member and the avulsing edge of the aperture between which avulsing edges protruding fatty tissue is entrapped and avulsed), prevents tenacious tissue caught therewithin having a tensile strength greater than the tensile strength of fatty tissue, from being avulsed. Tissue having a lower tensile strength which becomes entrapped within the avulsive portion of the cannula will be pulled apart by the shear force caused by the relative motion of the corrugated tissue-contacting avulsing edge of the rotating member pulling one surface of the tissue in the direction of rotation while the opposing surface of the entrapped tissue is held stationary against the avulsing edge of the cannula aperture by means of friction.

Prior art rotary devices have employed worm drives for connection of the drive motor to the rotary member within the cannula. Such worm drives permit reversible operation as well as oscillatory motion, but are more expensive and bulky and less energy efficient than straight through direct connection of the shaft of a rotary member to the drive shaft of the motor. The present device requires rotation of the auger in only a single direction for avulsing fatty tissue during lipectomy. Thus, there is no need for a (high profile)

worm drive gear train enabling the shaft of the rotary member to be releasably connected directly to the drive shaft of the rotary motor without power loss due to the heating of intervening gears in the power train. Although heat generation is reduced by direct coupling, the rotary motor within the handle portion of the device will generate heat. Such heat can be dissipated by means of a heat exchanger (not shown) mounted on the handle portion in thermal contact with the portion of the handle portion overlying the rotary motor. The heat exchanger may simply comprise an irrigation fluid flow channel or a radiating heat sink.

With reference now to FIG. 1, a perspective view of an embodiment 60 of the present invention is shown. The embodiment 60 of the rotary member comprises a flexible axial shaft 62 having an auger portion 63 thereon. The auger portion 63 comprises a spiral flange 64 extending laterally outward from an axial shaft 62. The outer tissue-contacting edge 65 of the flange 64 is preferably rounded or dull to prevent cutting tissue protruding through the overlying aperture in the outer tube of the cannula. In embodiment 60, the flexible shaft 62 is supported distally by means of a distal bearing 66. As the flexibly elastically deformable shaft 62 rotates within the outer tube of the cannula, tissue protruding into the aperture 19 in the outer cannula is captured within the cannula lumen. The rotating-tissue contacting surface of the auger together with the overlying avulsing edge of the aperture, avulses the tissue. If the tissue has too high a tensile strength, the flexible shaft 62 may bend or flex to permit the rounded tissue-contacting edge of the auger to slide over the captured tissue without avulsing it thereby permitting the captured tissue to escape from the avulsing portion of the cannula. An irrigation lumen 68 extends from the irrigation port 67 to the distal tip of the outer cannula and provides fluid communication therebetween.

In yet another embodiment of the present invention, the outer tube 71 of the cannula, shown in FIG. 7, has an aperture 72 in the wall 73 thereof which has an elastic material 74 affixed thereto. The elastic material 74 bordering the avulsing edge of the aperture 72 is sufficiently flexible so that an auger having a tissue-contacting surface rotating thereunder is unable to avulse tissue having tensile strength higher than that of fatty tissue the avulsing edge of the aperture 72 being elastically deformable, permitting the tissue-contacting edge of the auger (not shown) to turn past the aperture without avulsing the tissue. It is also highly desirable to provide a means for varying the elasticity of either the tissue contacting edge of the auger or the border of the cannula aperture. Providing such a means for varying the force required for avulsion provides the operator the ability to adjust the elasticity of the avulsing portion to minimize the amount of blood appearing and the aspirated avulsate. Such a tuning means for elastic deformation might, for example, comprise elongating the shaft of an elastic auger shaft to reduce the outer diameter thereby permitting slippage of tissue between the tissue-contacting edge of the rotating member and the avulsing edge of the cannula aperture.

Another means for varying the elastic deformation of the avulsing portion of the cannula is by supporting available portion of the elastic avulsing edge of the aperture 71 with a variable underlying, rigid member which may be adjusted to vary the flexibility of the overlying avulsing edge of the aperture. Such a construction however, requires more separable parts on the invasive portion of the cannula. From the manufacturing and safety standpoint, it is desirable that the outer cannula be a one piece rigid design to avoid intratissue fragmentation and residual foreign body effect.

The elastic deformation of the outer avulsing edges of the auger can readily be controlled by changing the aspect ratio (the ratio of the lateral projection of the flange from the central radial shaft member to the thickness and taper of the flange). For a particular flange composition, thinner flanges having a given lateral extension are more elastic than thicker flanges having the same lateral extension from the shaft of the auger.

Figure 8:
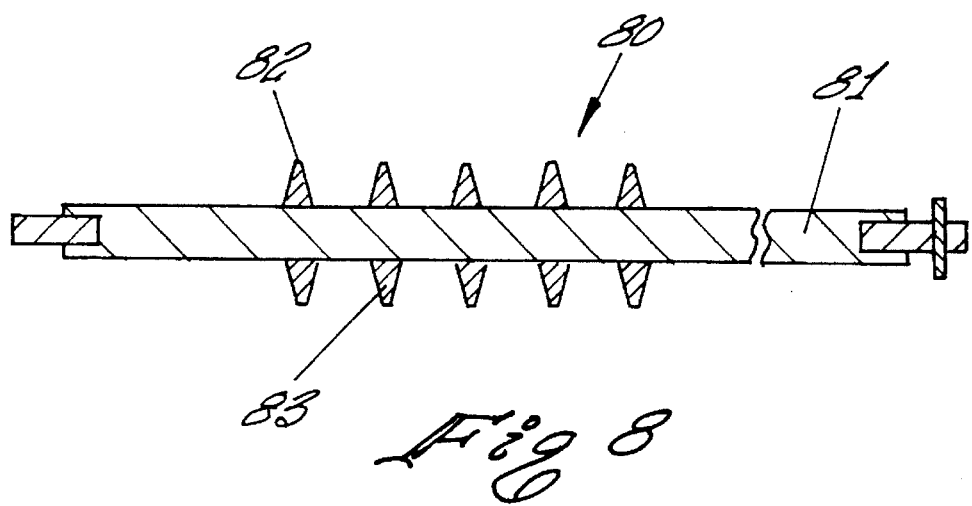
FIG. 8 is a cross-sectional side view of an embodiment of the rotary member of the cannula portion wherein the axial shaft supporting the tissue-contacting auger flange is flexible.

FIG. 8 shows a cross sectional view of yet another embodiment of the handpiece wherein the rotating member 80 has a flexible shaft. The flexible shaft 81 has a stainless steel spiral auger or angled discs 83 mounted thereupon. The rotary member 80 rotates within the outer tube (not shown in FIG. 5) of the apertured cannula as previously described. In operation, the tissue-contacting edge 82 of the rotating discs 83 stretch the tissue protruding or herniating into the aperture in the outer tube of the cannula, avulsing less tenacious tissue.

Figures 9A, 9B:
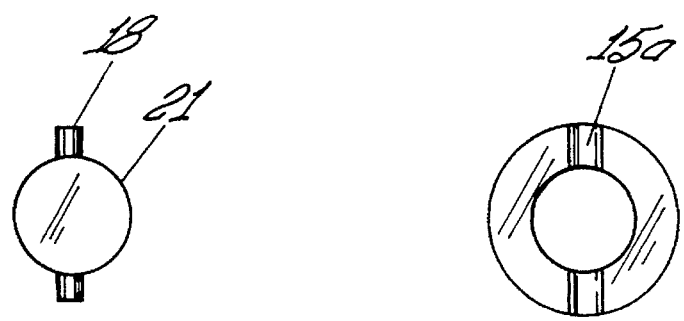

Examples of a means for releasably engaging the proximal end of the rotary member to the distal end of the motor drive shaft are shown in the FIGS. 9a and 9b. FIG. 9a shows the proximal end of the rotary member of the auger portion. FIG. 9b is an end view of the distal end of a drive shaft protruding from the rotary power source which distal end is adapted to releasably engage mating connection means on the proximal end of the rotary member.

The cannula portion of the handpiece in accordance with the teaching herein, is preferably made in different lengths and diameters for different suction-lipectomy applications. The overall diameter of the apertured outer tube of the cannula portion is preferably between 4 mm and 8 mm. Different sizes of cannulas are necessary because surgeons have different cannula preferences for performing suction lipectomy within different anatomical locations. As an example, the smaller cannulas have greater utilization for aspiration of fat under the neck, whereas larger, longer cannulas are used for abdominal fat aspiration as well as lateral thighs. The handpiece preferably has irrigation and aspiration ports integral therewith and operable for conducting irrigation solution to the cannula aperture as well as removing avulsed tissue from the cannula by vacuum aspiration as shown in FIG. 6. The irrigation port 67 and the suction or aspiration port 68 are preferably attached to and integral with the outer tube 14 of the cannula 12.

While particular embodiments of the present invention have been illustrated and described, it would be obvious to those skilled in the art that various other changes and modification can be made without departing from the spirit and scope of the invention. For example, the avulsing efficiency of an avulsing edge in accordance with the handpiece of the present invention may also be varied by changing the density, shape and length of the grooves on the avulsing edge or texture applied thereto. Similarly, the present handpiece can be advantageously used in combination with adjunctive means for enhancing the efficiency and selectivity of fat removal including ultrasonic perturbation of the target tissue either before or during liposuction or the administration of an agent which reduces the cohesiveness of fatty tissue with respect to the cohesiveness of non-fatty associated tissue. It is therefore intended to cover in the appended claims all such changes and modifications that are within the scope of this invention.

What I claim is:

1. A power assisted suction lipectomy device operable for removing fatty tissue from beneath the skin of a patient, said device comprising a non-invasive handle portion housing A source of rotary power and having a proximal end and a distal end, said distal end having cannula connection means thereon, and an invasive cannula portion comprising:

(a) a rigid hollow elongate outer tube having an inner lumen, a proximal end adapted to matingly engage and releasably attach said outer tube to said cannula connection means on said distal end of said handle portion and a distal end and a cylindrical surface therebetween, said cylindrical surface having an aperture therein, the edge of said aperture providing a stationary avulsing edge.

(b) a rotating member rotatably mounted coaxially within said inner lumen of said rigid outer tube comprising an elongate shaft having a proximal end adapted to mechanically engage said source of rotary power and a distal end and a shaft therebetween, said shaft having a spiral flange projecting laterally therefrom, the outermost lateral extension of said spiral flange being a rotating avulsing edge, and wherein a portion of said rotating avulsing edge adjacent to said stationary avulsing edge is adapted to elastically deform in response to pressure applied thereto.

2. A handpiece for a suction lipectomy device operable for removing unwanted fatty tissue from beneath the skin of a patient, the handpiece comprising:

(a) a handle portion having a proximal end and a distal end and source of rotary power housed therewithin; and (b) a cannula portion, said cannula portion further comprising:

(i) an elongate outer tube having a rigid cylindrical wall enclosing a cylindrical cannula lumen, said cannula having a proximal end with attachment means operable for rigidly attaching said cannula to said distal end of said handle portion and having at least one aperture in said cylindrical wall; and (ii) a rotary member housed within said cannula lumen wherein an avulsing portion of said rotary member underlies said at least one aperture in said cylindrical wall and wherein said avulsing portion of said rotary member comprises a helical flange projecting laterally from an elongate shaft along a portion of the length thereof and wherein said flange has an outer edge which is elastically deformable.

3. A power assisted suction lipectomy device comprising a handpiece, said handpiece further comprising:

(a) a handle portion having a power driven movable drive shaft therewithin; and (b) a cannula portion wherein said cannula portion further comprises:

i) a rigid hollow outer tube having a proximal end adapted to releasably connect to said handle portion, and a distal end and a cylindrical outer surface having an aperture therein wherein said aperture has an avulsing edge comprising an elastically deformable material; and ii) a movable member disposed within said outer tube having a proximal end adapted to releasably engage said drive shaft and a distal end and a elongate shaft movable edge therebetween wherein at least a portion of said movable edge underlies said aperture in said outer tube.

4. The power assisted suction lipectomy device in accordance with claim 3 wherein said movable edge is elastically deformable.

5. The power assisted suction lipectomy device in accordance with claim 4 wherein said stationary edge is rigid.

* * * * *